United States Patent
Sienkiewicz et al.

[11] Patent Number: 5,803,902
[45] Date of Patent: Sep. 8, 1998

[54] SURGICAL RETRACTOR

[75] Inventors: Henry R. Sienkiewicz, Stamford; Robert C. Savage, Stratford; Stanley J. Malinowski, Guilford; Douglas M. Dunklee, Bridgeport; Henry Holsten, Wolcott, all of Conn.

[73] Assignee: United States Surgical Corporation, Norwalk, Conn.

[21] Appl. No.: 710,747

[22] Filed: Sep. 20, 1996

Related U.S. Application Data

[63] Continuation-in-part of Ser. No. 319,172, Oct. 6, 1994, Pat. No. 5,656,012.

[51] Int. Cl.$^6$ ..................................................... A61B 11/02
[52] U.S. Cl. .......................... 600/203; 600/201; 600/204; 128/853
[58] Field of Search ..................................... 600/102, 201, 600/203, 204; 206/569, 570, 571, 363, 364, 365, 366, 438, 439, 440, 441, 819; 128/853

[56] References Cited

U.S. PATENT DOCUMENTS

| | | |
|---|---|---|
| 832,201 | 10/1906 | Kistler . |
| 1,271,456 | 7/1918 | Flack . |
| 1,275,520 | 8/1918 | Bell . |
| 1,947,649 | 2/1934 | Kadavy . |
| 3,495,586 | 2/1970 | Regenbogen . |
| 4,190,042 | 2/1980 | Sinnreich . |
| 5,002,070 | 3/1991 | Taylor ..................................... 128/853 |
| 5,080,088 | 1/1992 | Levahn . |
| 5,113,846 | 5/1992 | Hiltebrandt . |
| 5,178,133 | 1/1993 | Pena ........................................ 600/203 |
| 5,195,506 | 3/1993 | Hulfish . |
| 5,195,507 | 3/1993 | Bilweis . |
| 5,235,966 | 8/1993 | Jamner . |
| 5,275,610 | 1/1994 | Eberback . |
| 5,279,539 | 1/1994 | Bohan et al. . |
| 5,315,985 | 5/1994 | Decarie et al. .......................... 600/101 |
| 5,318,012 | 6/1994 | Wilk . |
| 5,318,586 | 6/1994 | Ereren . |
| 5,325,848 | 7/1994 | Adams et al. . |
| 5,339,803 | 8/1994 | Mayzels et al. . |
| 5,345,927 | 9/1994 | Bonutti . |
| 5,351,679 | 10/1994 | Mayzels et al. . |
| 5,358,496 | 10/1994 | Ortiz et al. . |
| 5,441,044 | 8/1995 | Tovey et al. . |
| 5,542,539 | 8/1996 | Early ....................................... 206/499 |

*Primary Examiner*—Beverly M. Flanagan

[57] ABSTRACT

A surgical retractor is disclosed having a handle portion, an elongated body portion extending distally from the handle portion and including an outer tube, a stabilizing member extending from a distal end of the outer tube and a pair of resilient bands pivotably connected to a distal end portion of the stabilizing member. An actuation mechanism is provided which is associated with the handle portion and the resilient bands for moving the bands between open and closed position. The surgical retractor further includes a sheath dimensioned to receive at least a portion of the stabilizing member and the bands. A surgical kit is also provided having a package configured to receive a surgical instrument, a base member for sealing the package, a surgical instrument having proximal and distal ends and having a mechanism for performing a surgical procedure located at the distal end, and a static barrier for enclosing the mechanism of the surgical retractor.

10 Claims, 15 Drawing Sheets

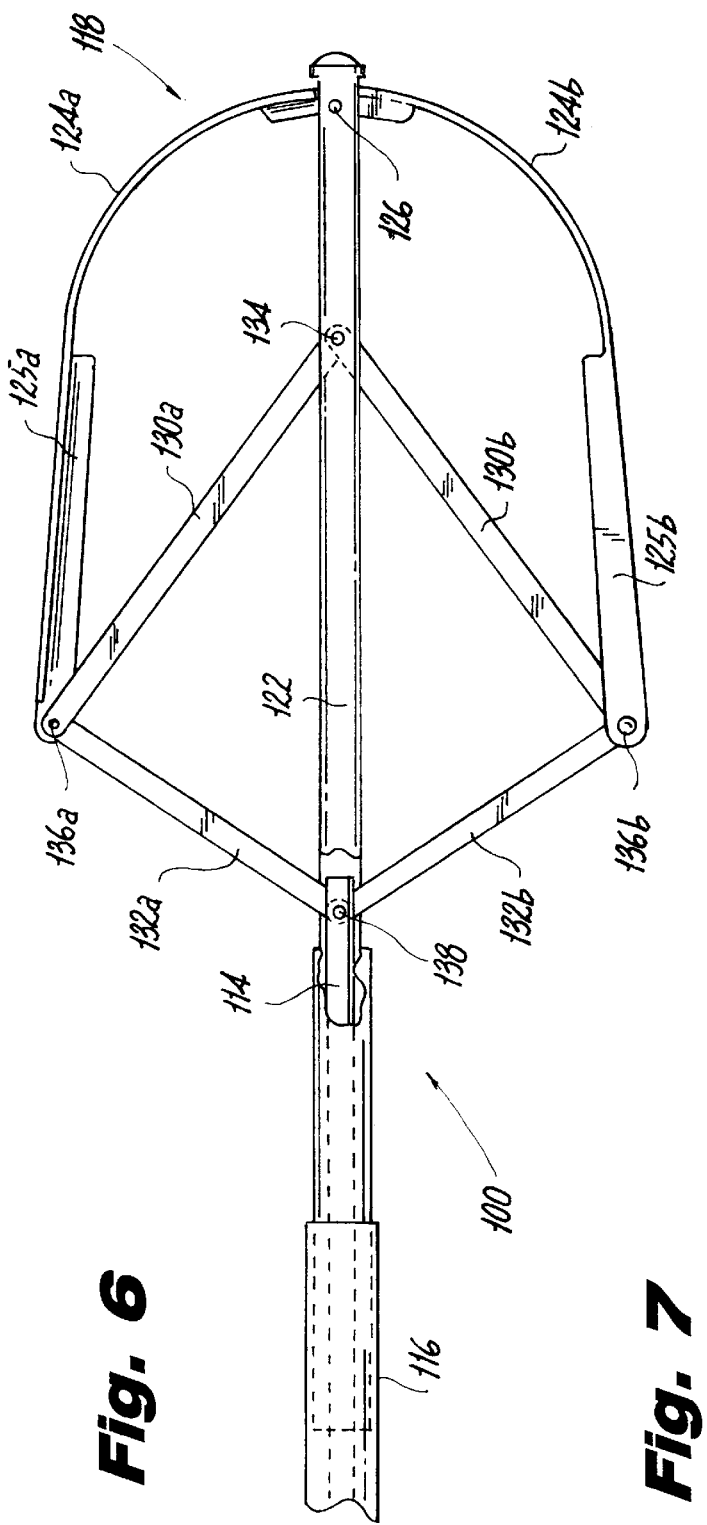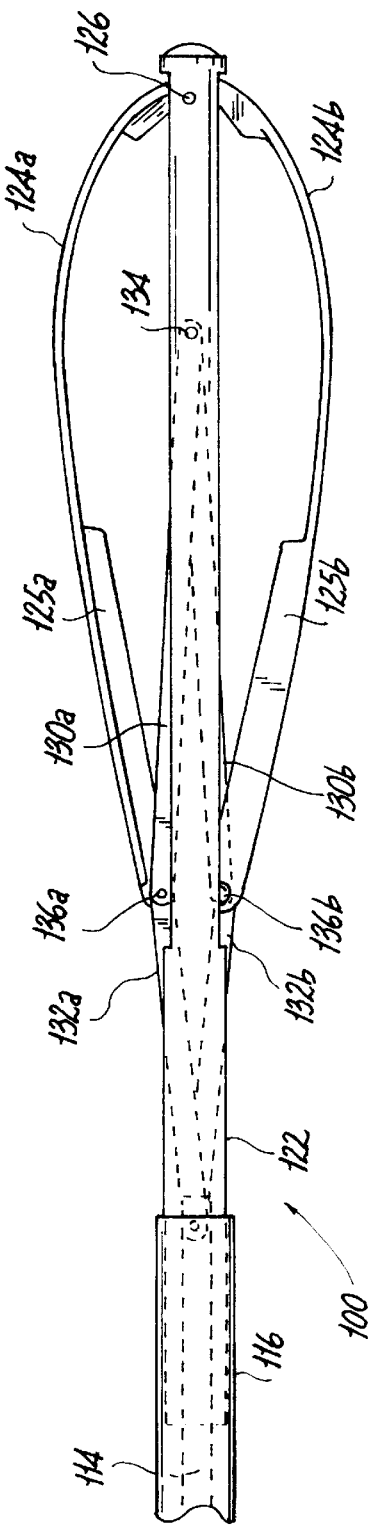

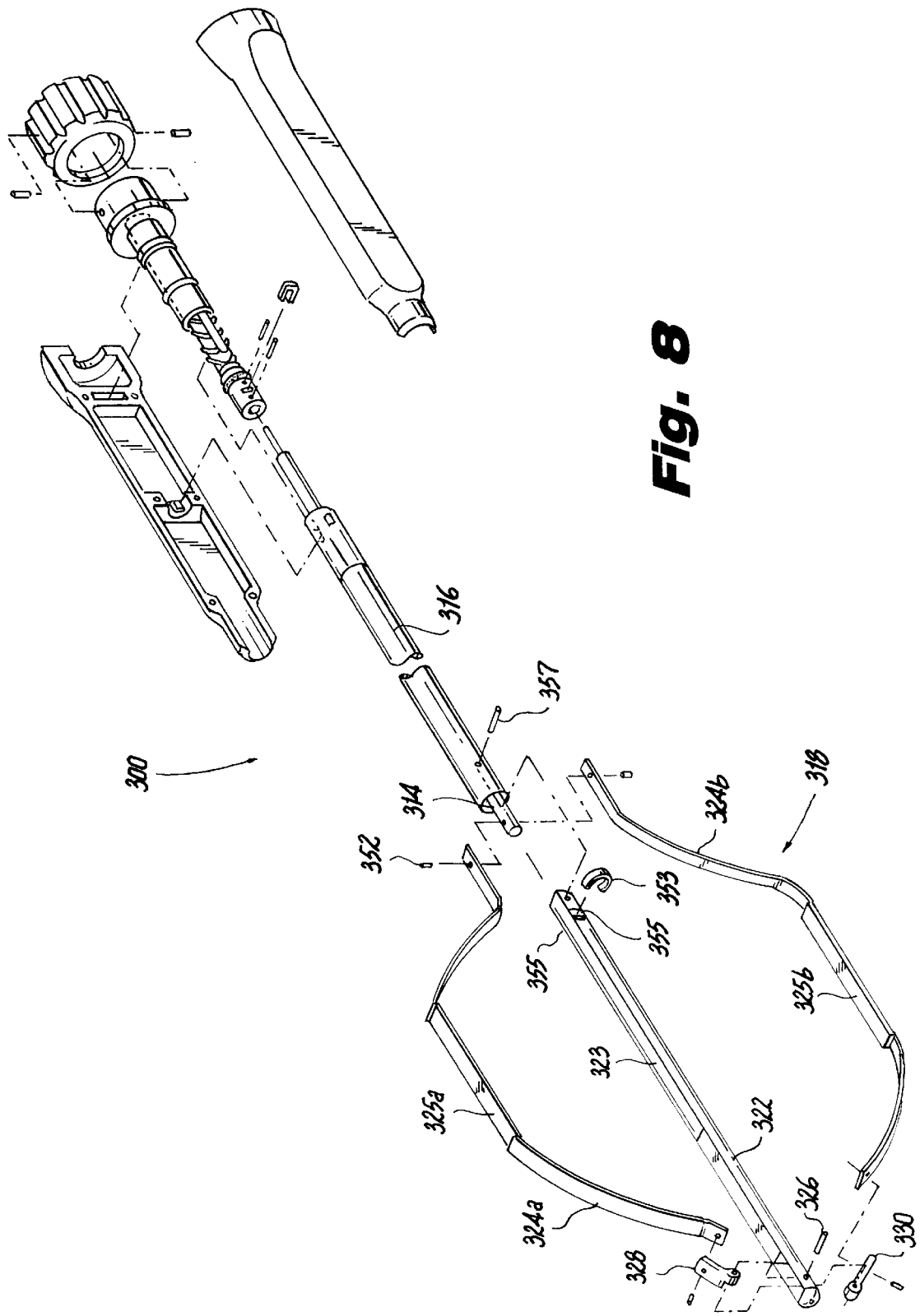

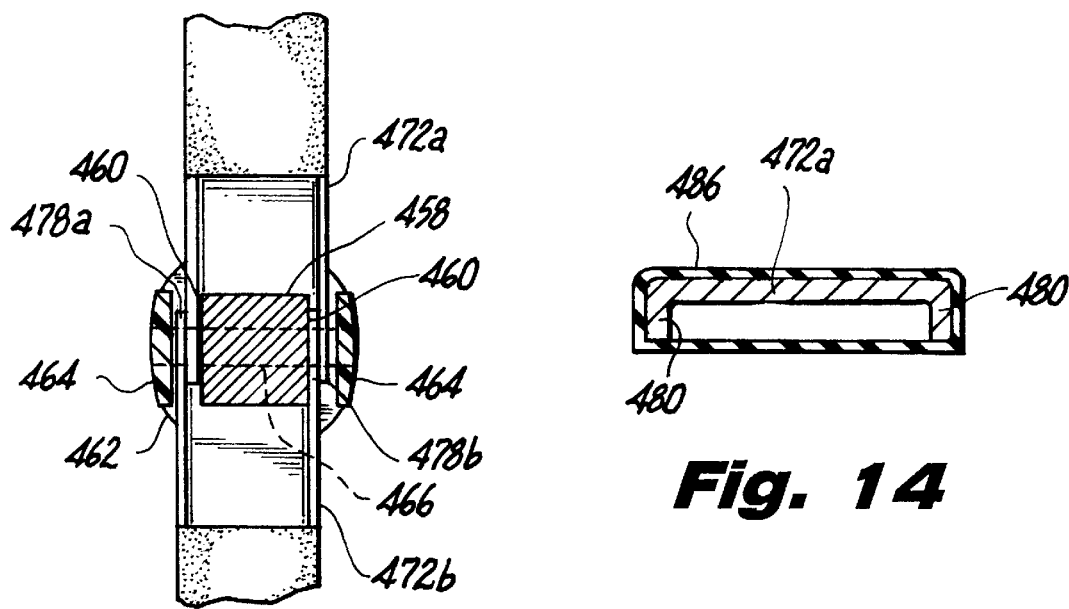
Fig. 14
Fig. 15
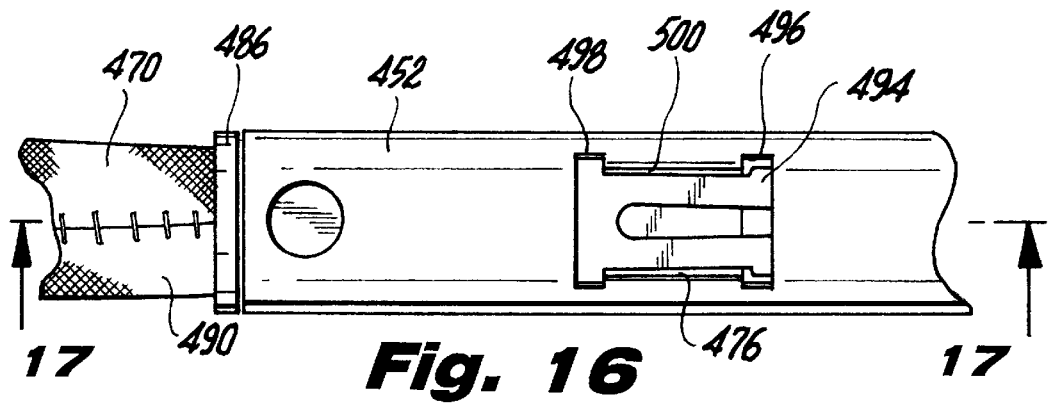
Fig. 16
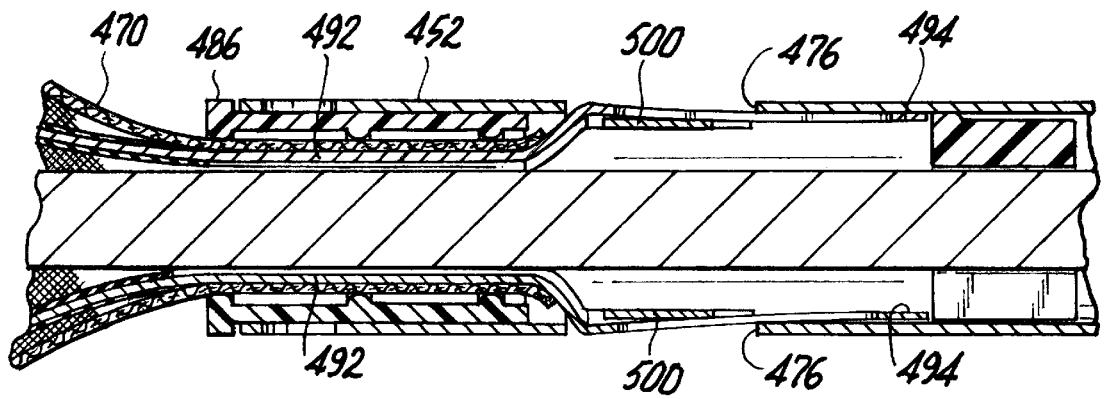
Fig. 17

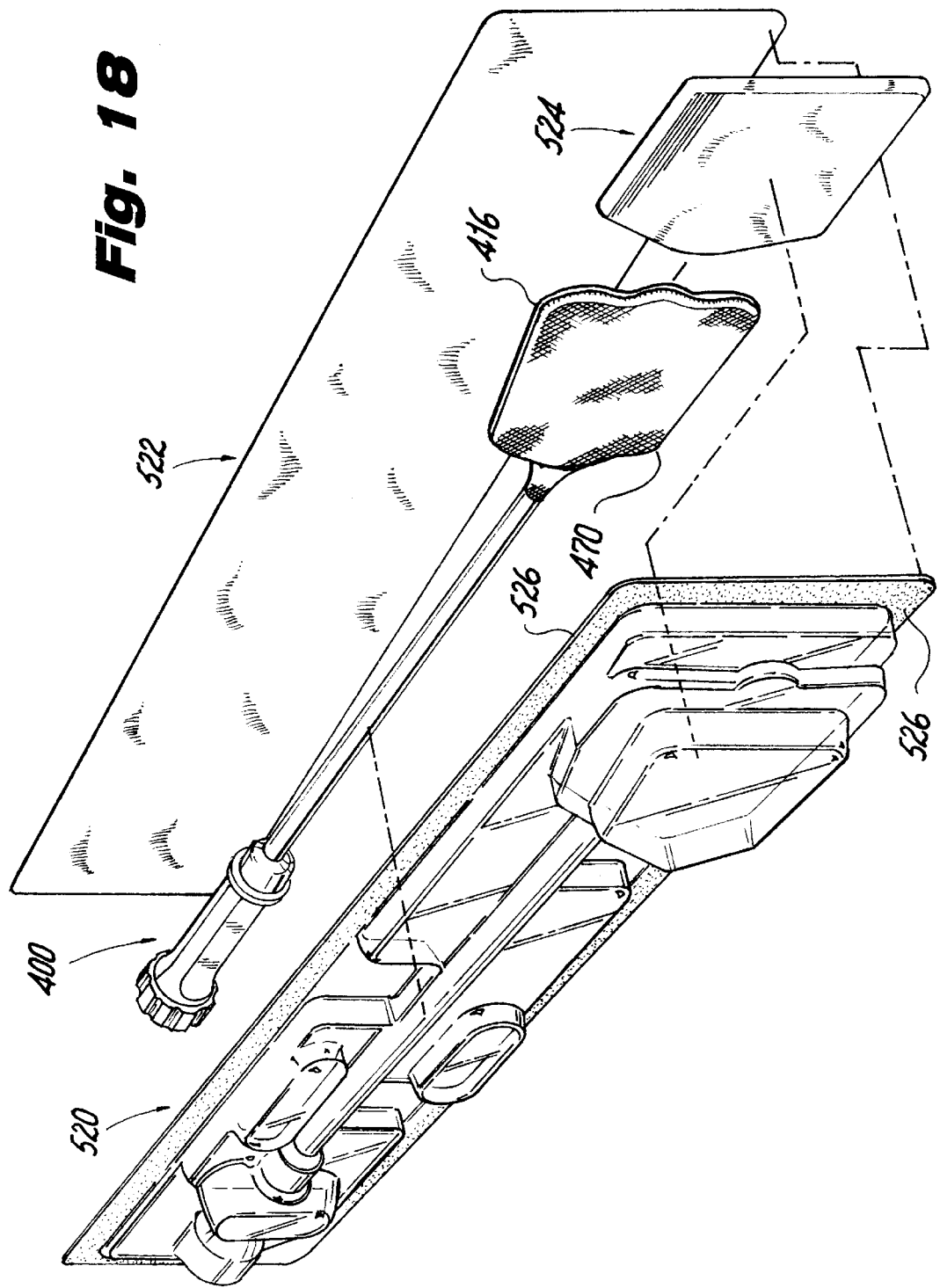

SURGICAL RETRACTOR

CROSS-REFERENCE TO RELATED APPLICATIONS

This application is a continuation-in-part of Appln. Ser. No. 08/319,172, filed Oct. 6, 1994, now U.S. Pat. No. 5,656,012.

BACKGROUND

1. Technical Field

This application relates to surgical instrumentation, and more particularly, to a surgical retractor having an expandable sheath which defines a retraction surface for manipulating tissue and organs during endoscopic or laparoscopic surgical procedures.

2. Description of Related Art

In conventional surgical procedures the function of holding tissue and organs in a given location to facilitate access and viewing is typically accomplished by a retractor. The instrumentation is typically in the form of a broad paddle structure or multiple fingers attached to a handle. See, for example, U.S. Pat. No. 3,467,079 to James. One disadvantage of these methods is the requirement of making large incisions, often through major muscles, in order to manipulate the above instrumentation in the body cavity.

Endoscopic or laparoscopic procedures overcome many of the drawbacks of conventional surgery. Such procedures are characterized by the provision of an elongated cannula structure having a relatively small diameter with a proximal and distal end. The distal end is passed through the surrounding tissue into a body cavity via an incision in the body wall. The body cavity is typically inflated or "insufflated" with carbon dioxide gas to aid in viewing and accessing the surgical site. The cannula provides a conduit for insertion of surgical instrumentation into the cavity. These procedures allow for smaller incisions, shorter patient recovery periods and require less anesthesia than conventional methods.

Although the insufflation gas expands the abdomen to permit the surgeon to view the surgical site, it is often necessary to manipulate the internal organs or tissues to provide a clear path to the surgical objective. In the prior art, it has been known to utilize grasping tools which pull on the organs or tissues to move them out of the way to provide a clear visual path for the surgeon. However, these devices may damage the organ or tissues which they grasp, and consequently these devices are utilized only when absolutely necessary. In order to avoid the problems associated with grasping tools, endoscopic retractor mechanisms have been developed which are utilized to push and hold the tissue or organs away from the surgical site. Typically, these devices include paddles and/or fingers which expand after the retractor has been inserted into the abdomen through the trocar cannula. Such devices are disclosed in, for example, U.S. Pat. No. 4,654,028 to Suma, U.S. Pat. No. 4,909,789 to Taguchi et al., and U.S. Pat. No. 5,195,505 to Josefsen. Other retractor devices include collapsible fingers joined by webs of resilient material which expand to form the retractor. These devices are disclosed in, for example, U.S. Pat. No. 4,190,042 to Sinnreich and U.S. Pat. No. 4,744,363 to Hasson. Other devices include retractors having expandable frames for supporting expandable latex sheaths or covers, such as that described in U.S. Pat. No. 5,178,133 to Pena.

While one or more of the aforementioned devices have been successfully used in laparoscopic procedures, larger organs, such as the intestine and/or stomach, tend to be too large and too heavy to be properly supported by these retractors. Consequently, the retractors have difficulty in clearing the surgical field to provide access for the surgeon to the surgical site. Due to the small size of the instrumentation, particularly the trocar cannula through which these instruments must pass, it is difficult to provide a retractor mechanism which can support or otherwise manipulate large and pliable organs such as the intestines or stomach.

Therefore, a need exits for a retractor mechanism which may be utilized to manipulate large organs and that is reliable as far as the strength and durability of the instrument is concerned. A need also exists for a retractor instrument that can clear the surgical site of heavy organs and tissue, where the instrument is small in relation to the organ and can be utilized with conventional trocar cannulas to provide access to the site during an endoscopic or laparoscopic surgical procedure.

SUMMARY

A surgical retractor is provided that includes a stabilizing member defining a longitudinal axis and having a distal end portion, and at least one band member or arm having a distal end portion connected to the distal end portion of the stabilizing member and movable between an open position and a closed position. The band member may include a strengthening rib which provides the dual function of strengthening the band member to prevent flexure and controlling the shape of the band in an expanded condition. The retractor preferably further includes a tubular sheath dimensioned to receive the stabilizing member and the band member, and is configured to expand when the band member is moved from the closed position to the open position. The surgical retractor is further provided with a mechanism for selectively moving the band member between the open position and the closed position.

In a preferred embodiment, the surgical retractor includes an elongated outer tube, two band members or arms, a stationary stabilizing member extending distally from a distal end of the outer tube, a sheath disposed about the band members and the stabilizing member and a mechanism for moving the band members between an open position and a closed position. The sheath is preferably fixed to the distal end of the outer tube and is expandable by manipulation of the band moving mechanism.

In use, the bands and heath are collapsed and passed through a previously placed cannula in the body. An optional cover tube can be used to facilitate passage of the sheath through the cannula. Once the sheath and arms are disposed in the body cavity, the arm moving mechanism is manipulated to expand the arms and sheath. If a cover tube is used, the tube is withdrawn proximally prior to expansion. The combination of the arms, sheath and stabilizing member provide a retractor surface that can be used to manipulate organs or tissue. To withdraw the device, the arms are collapsed and the instrument is pulled out of the cannula. Since the sheath is preferably flexible, the sheath is easily removed, i.e., without use of the optional cover tube. Alternatively, if a cover tube is used, the tube can be advanced distally over the sheath prior to removal.

A surgical retractor kit is also provided that includes a package having indentations for receiving a surgical retractor, a base member for enclosing the package and a static barrier for enclosing the retractor assembly. The static barrier prevents static electric buildup on the tubular sheath of the surgical retractor.

BRIEF DESCRIPTION OF THE DRAWINGS

Various embodiment are described herein with reference to the drawings wherein:

FIG. 6 is a side elevational view of the retractor assembly of FIG. 5 in an open position, shown with the sheath removed;

FIG. 7 is a side elevational view of the retractor assembly of FIG. 5 in a substantially closed position, shown with the sheath removed;

FIG. 8 is an exploded perspective view of a preferred embodiment of a surgical retractor without a sheath;

FIG. 14 is a cross-sectional view taken along line 14—14 of FIG. 13;

FIG. 15 is a cross-sectional view taken along line 15—15 of FIG. 13;

FIG. 16 is a top view of the connection assembly of the surgical retractor of FIG. 10 connecting the resilient bands and tubular sheath to the outer tube;

FIG. 17 is a cross-sectional view taken along lines 17—17 of FIG. 16;

FIG. 18 is a perspective view of a surgical kit with parts separated;

DETAILED DESCRIPTION OF PREFERRED EMBODIMENTS

Figure 1:
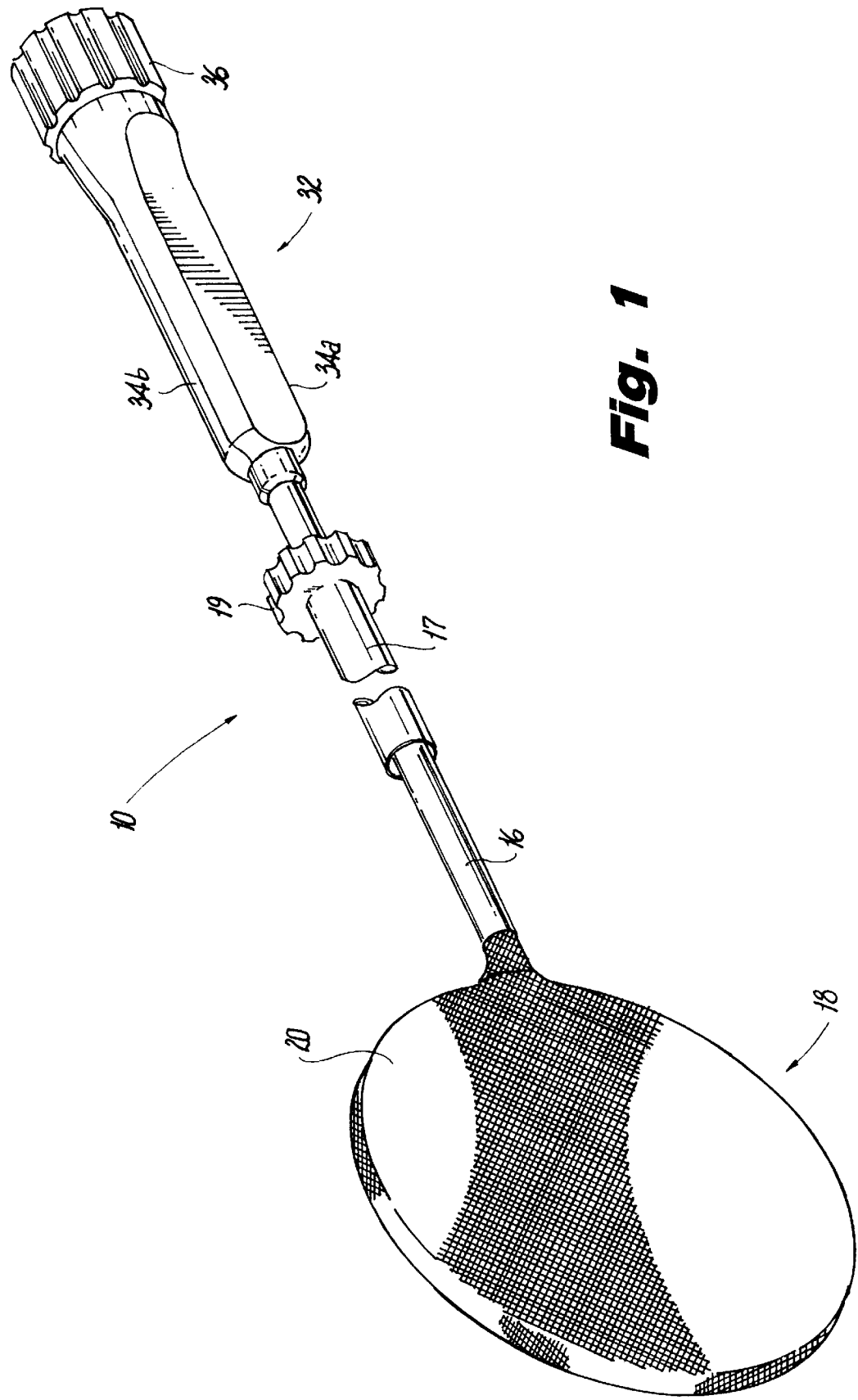
FIG. 1 is a perspective view of a surgical retractor constructed in accordance with a preferred embodiment and disposed in an open position.

In the drawings and in the description which follows, the term "proximal", as is traditional, will refer to the end of the apparatus which is closest to the operator, while the term "distal" will refer to the end which is furthest from the operator.

The present apparatus hall be discussed in terms of endoscopic procedures and apparatus. However use herein of terms such as "endoscopic", "endoscopically", and "endoscopic portion", among others, should not be construed to limit the present disclosure to an apparatus for use only in conjunction with an endoscopic tube. To the contrary, it is believed that the present apparatus may find use in procedures wherein access is limited to a small incision including but not limited to endoscopic, arthroscopic and/or laparoscopic procedures.

Referring to FIG. 1, there is illustrated a unique surgical retractor constructed in accordance with a preferred embodiment designated generally by reference numeral 10. Surgical retractor 10 includes an elongated body portion which includes an outer tube 16 having proximal and distal end portions, an expandable retractor assembly 18 covered by an expandable tubular sheath 20 located at the distal end of tube 16, and a handle assembly 32 located at the proximal end of tube 16. The expandable retractor 18 is progressively deployed by an actuator mechanism that includes adjusting knob 36 provided at the proximal end portion of handle 32. Also shown in FIG. 1 is optional cover tube 17 disposed about outer tube 16. Cover tube 17 has gripping member 19 associated therewith to facilitate longitudinal (distal-proximal) movement along outer tube 16.

Figure 2:
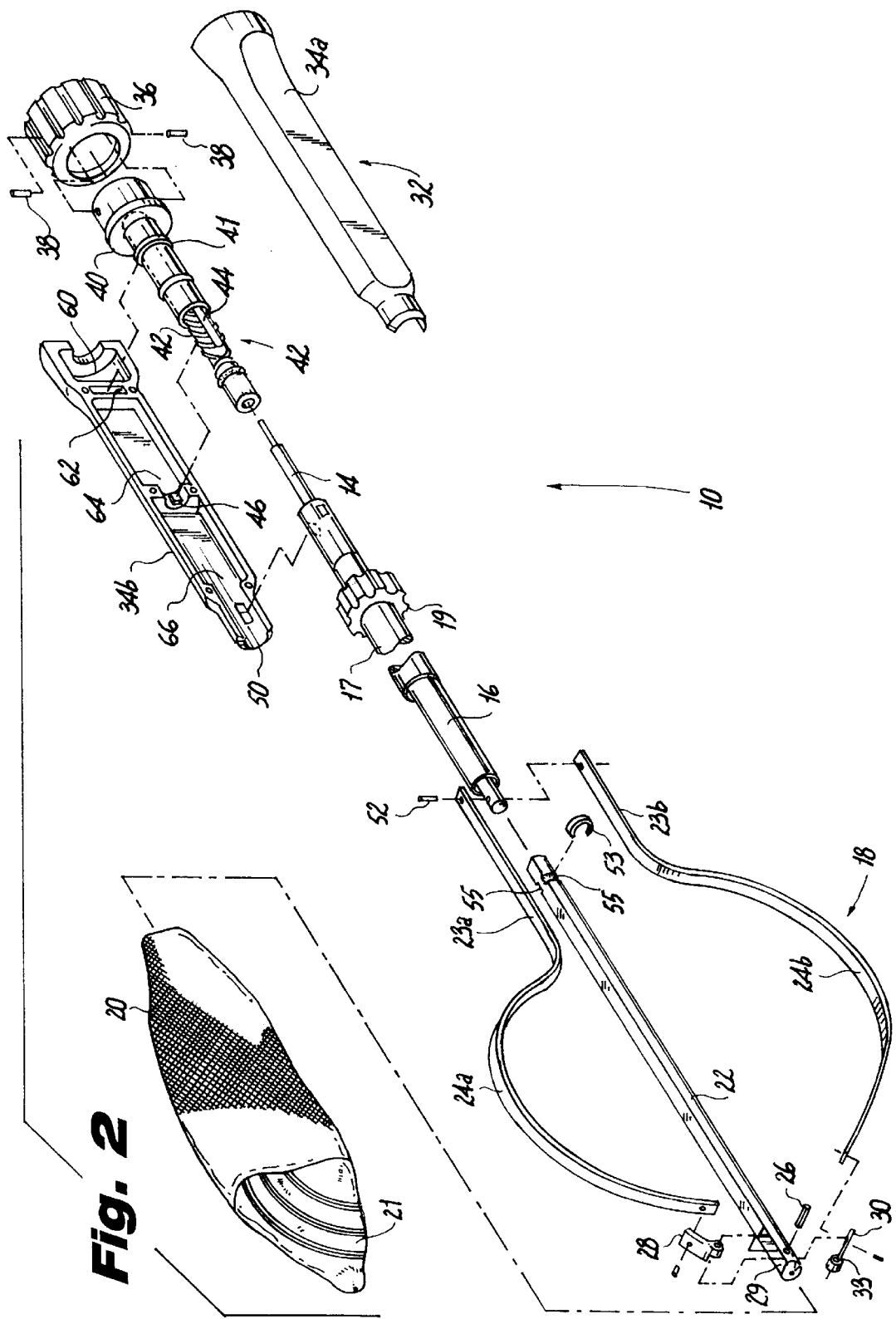
FIG. 2 is an exploded perspective view of the surgical retractor of FIG. 1.

Turning to FIG. 2, retractor assembly 18 consists of a stabilizing member (or center member) 22 oriented along a longitudinal axis which provides support to the retractor assembly 18 during the manipulation of organ structures or other body tissue. A distal end portion of the stabilizing member 22 is provided with a convex tip to inhibit puncturing of tubular sheath 20 and to prevent trauma to internal tissue and organs during insertion. A pair of resilient band members 24a and 24b are pivotably mounted at the distal end portion of stabilizing member 22 by hinge members 28 and 30, respectively attached to the distal end portions of the resilient bands 24a and 24b. Hinge members 28 and 30 are dimensioned to be received within slot 29 formed at the distal end portion of stabilizing member 22 and are pivotably retained therein by pivot pin 26 which passes through radial bore 31 formed in stabilizing member 22 and bores 33 in each hinge member. Proximal ends 23a and 23b of hinge members 28 and 30 are pinned by pin 52 to the distal end of rod 14, which is longitudinally slidable within outer tube 16.

Resilient bands 24a and 24b are preferably formed of stainless steel or other flexible resilient material, such as shape memory alloy or a flexible polymer, the configuration of which can be controlled mechanically by applying a stress to the material. In the present embodiment, the resilient bands are movable between an open, deployed configuration and a closed retracted position. In the deployed position, the shape of each of the resilient bands 24a and 24b is preferably an arcuate configuration. In the retracted position, resilient bands 24a and 24b are substantially straight and extend proximally from the distal pivotable hinge point and are in close approximation with stabilizing member 22 along the length of the resilient bands. The resilient bands 24a and 24b are preferably fabricated with a rectangular cross-section to strengthen the bands in the deployed position. Alternatively, the cross-section may be semicircular or other suitable configuration.

The expandable sheath 20 is preferably fabricated from a textile material such as surgical mesh, cloth, nylon, etc., and configured to enclose the stabilizing member 22 and the resilient bands 24a and 24b. Alternatively, sheath 20 can be fabricated from an elastomeric material such as, for example, latex. The proximal end of sheath 20 is preferably retained between locking collar 53 and proximal notches 55 formed on stabilizing member 22. When assembled, locking collar 53 and the proximal end of stabilizing member 22 are inserted into the distal end of outer tube 16 and are held in a fixed position relative to tube 16 by friction fit or other means, i.e., glue, pins or the like. Bands 24a and 24b are also disposed in sheath 20 and are slidable relative to the stabilizing member so as to permit expansion within the sheath. In the deployed position of the resilient bands as described hereinabove, sheath 20 is expanded so as to define a retracting surface for manipulating body tissue and organs during laparoscopic or endoscopic surgical procedure. Reinforcing ribs 21 may be provided in the sheath 20 to aid in resisting deformation or tearing of the retraction surface during surgical manipulation.

Figure 3:
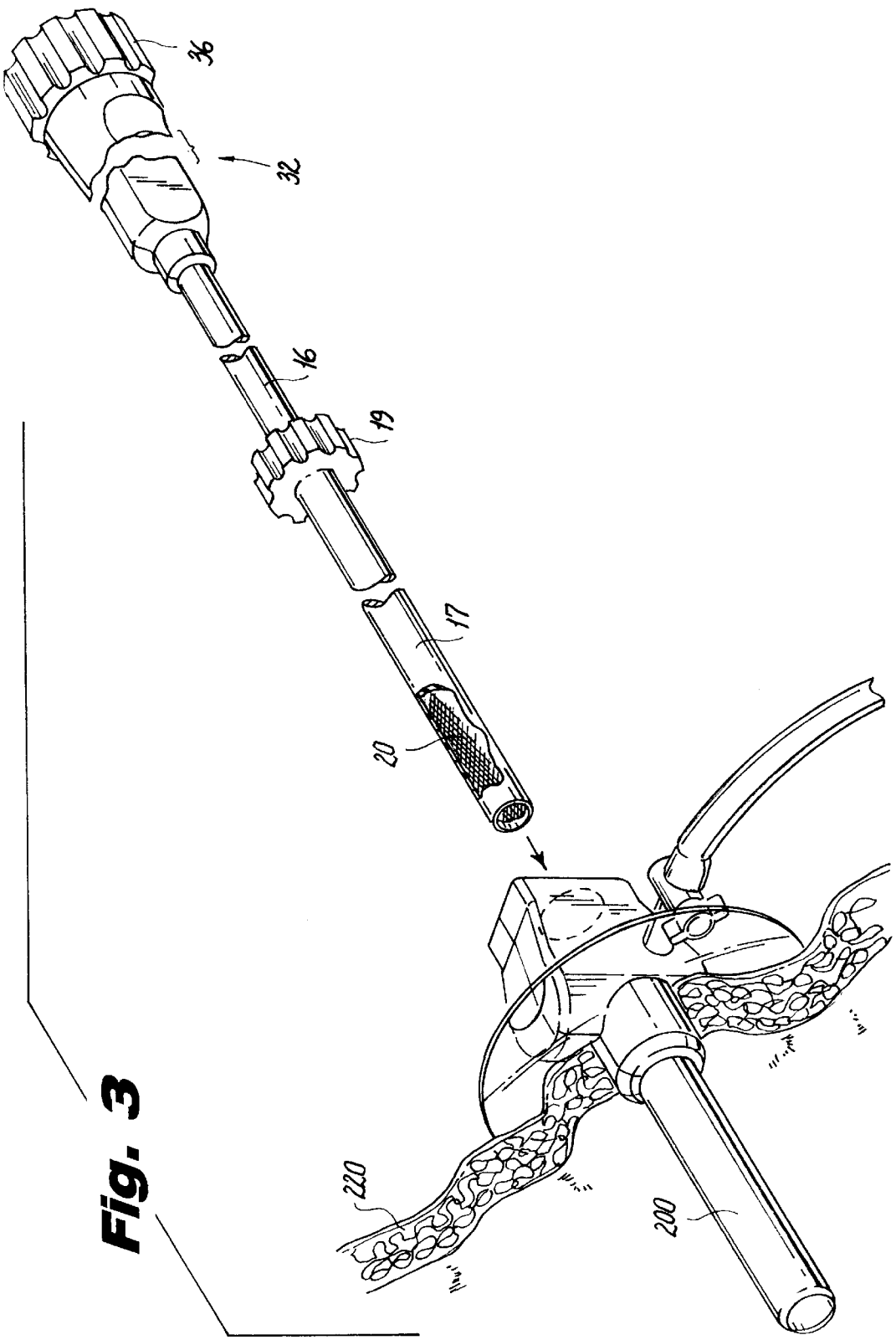
FIG. 3 is a perspective view of the surgical retractor of FIG. 1 in the closed position approaching a cannula.

When collapsed, retractor assembly 18 is dimensioned to be received within cover tube member 17 when the tube is advanced distally (see FIG. 3). The proximal end of cover tube 17 has grasping surface 19 to facilitate longitudinal movement of the tube.

With continued reference to FIG. 2, the handle portion 32 includes right and left hemi-sections 34a and 34b having a stepped longitudinal bore 50 extending therethrough defined by a proximal chamber 60, circumferential groove section 62, medial chamber 64, and distal chamber 66. Handle portion 32 houses an actuator mechanism for manipulating retractor assembly 18. The proximal portion of outer tube 16 is connected to the distal portion of handle 32 and the longitudinal bore of tube 16 is coaxial with longitudinal bore 50 of handle 32.

The actuator mechanism includes rotatable knob 36, rotatable screw housing member 40, and axially advanceable driving screw 42. The distal end of screw 42 is provided with a longitudinal bore for receiving the proximal end portion of driving rod 14 which is slidably received in outer tube 16. The distal end portion of driving rod 14 is connected to bands 24a and 24b by pin 52 as described above. Knob 36 is rigidly affixed to rotatable screw housing member 40 by retaining pin 38 and rotates coaxially therewith. Rotatable screw housing member 40 is formed with an internal threaded bore extending at least partially therethrough for operatively engaging driving screw 42. Screw housing member 40 is also formed with an annular mounting flange 41 dimensioned for engagement in the circumferential groove 62 of handle sections 34a and 34b. Driving screw 42 is preferably provided with a longitudinal slot 44 for accommodating a longitudinal engaging boss 46 formed within longitudinal bore 50 of handle section 34. The engagement of boss 46 in longitudinal slot 44 restrains driving screw 42 to longitudinal displacement only, such that axial rotation of the coupled knob 36 and rotatable screw member 40 effects corresponding longitudinal displacement of driving screw 42, driving rod 14. Longitudinal movement of rod 14 controls the deployment of bands 24a and 24b within sheath 20. The function of displacing driving rod 14 distally may be alternatively performed by a sliding handle mechanism.

Figure 4:
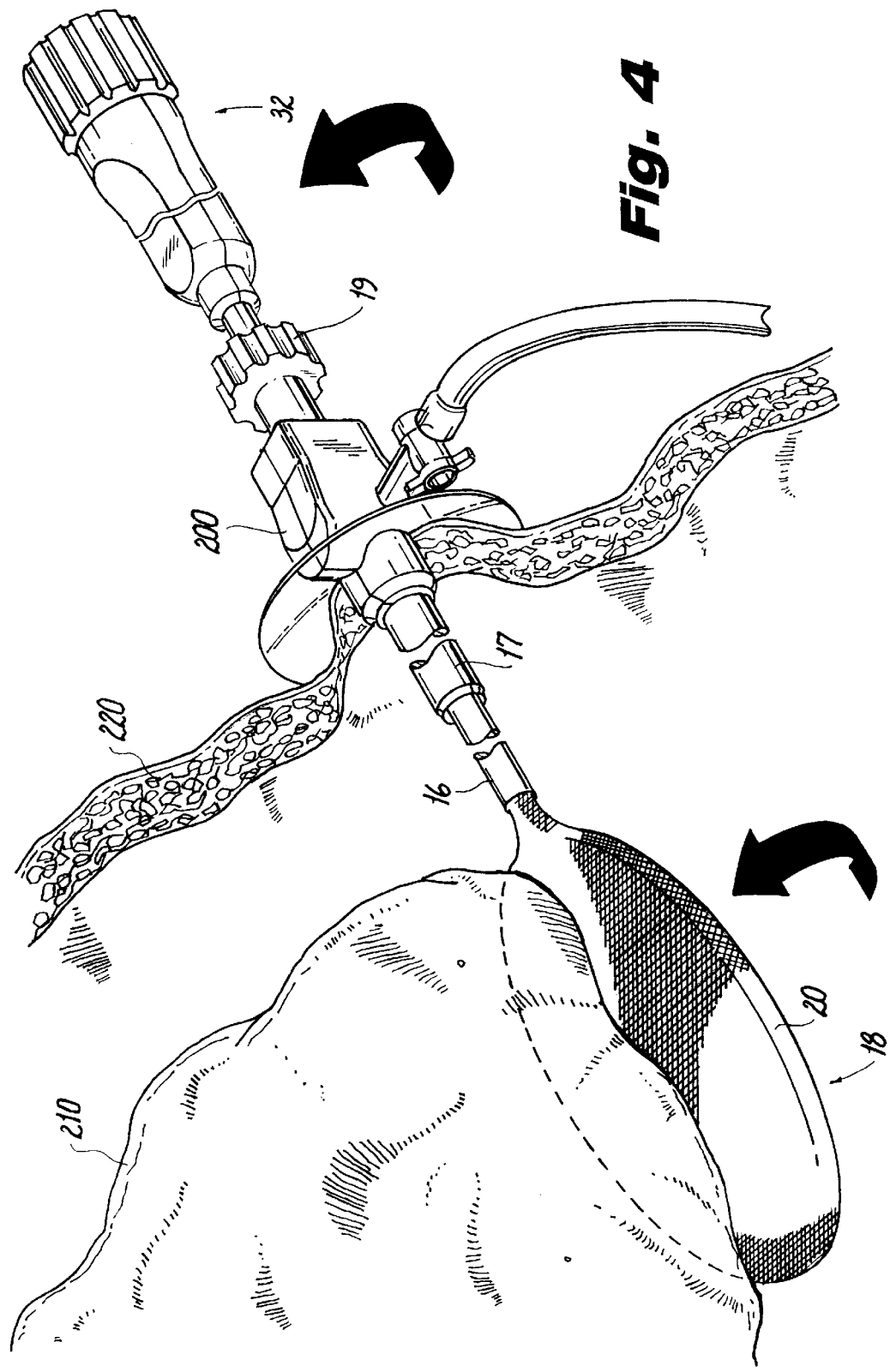
FIG. 4 is a perspective view of the surgical retractor disposed within a cannula in the body cavity.

Referring to FIGS. 3–4, use of retractor 10 is illustrated. Cannula 200 is inserted through body wall 220 at the operative site to access tissue or organs 210. In the retracted position illustrated in FIG. 3, stabilizing member 22, bands 24a and 24b and sheath 20 are disposed in cover tube 17. In this configuration, the distal end of instrument 10 can be easily inserted through cannula 200. Turning to FIG. 4, cover tube 17 has been slid proximally to expose retractor assembly 18. Knob 36 has been rotated to move center rod 14 distally thereby causing resilient bands 24a and 24b to move distally and expand within sheath 20. Distal movement of rod 14 terminates upon contact with the proximal end of stabilizing member 22.

During a typical laparoscopic or endoscopic surgical procedure, several trocar tubes 200 can be inserted to accommodate an endoscope for viewing and other instruments to carry out the procedure. Upon completion of the procedure, the surgeon can collapse retractor assembly 18 by rotating knob 36. Retractor 10 then may be withdrawn from the trocar. If cover tube 17 is used, it can optionally be advanced distally to cover assembly 18 prior to withdrawal.

Figure 5:
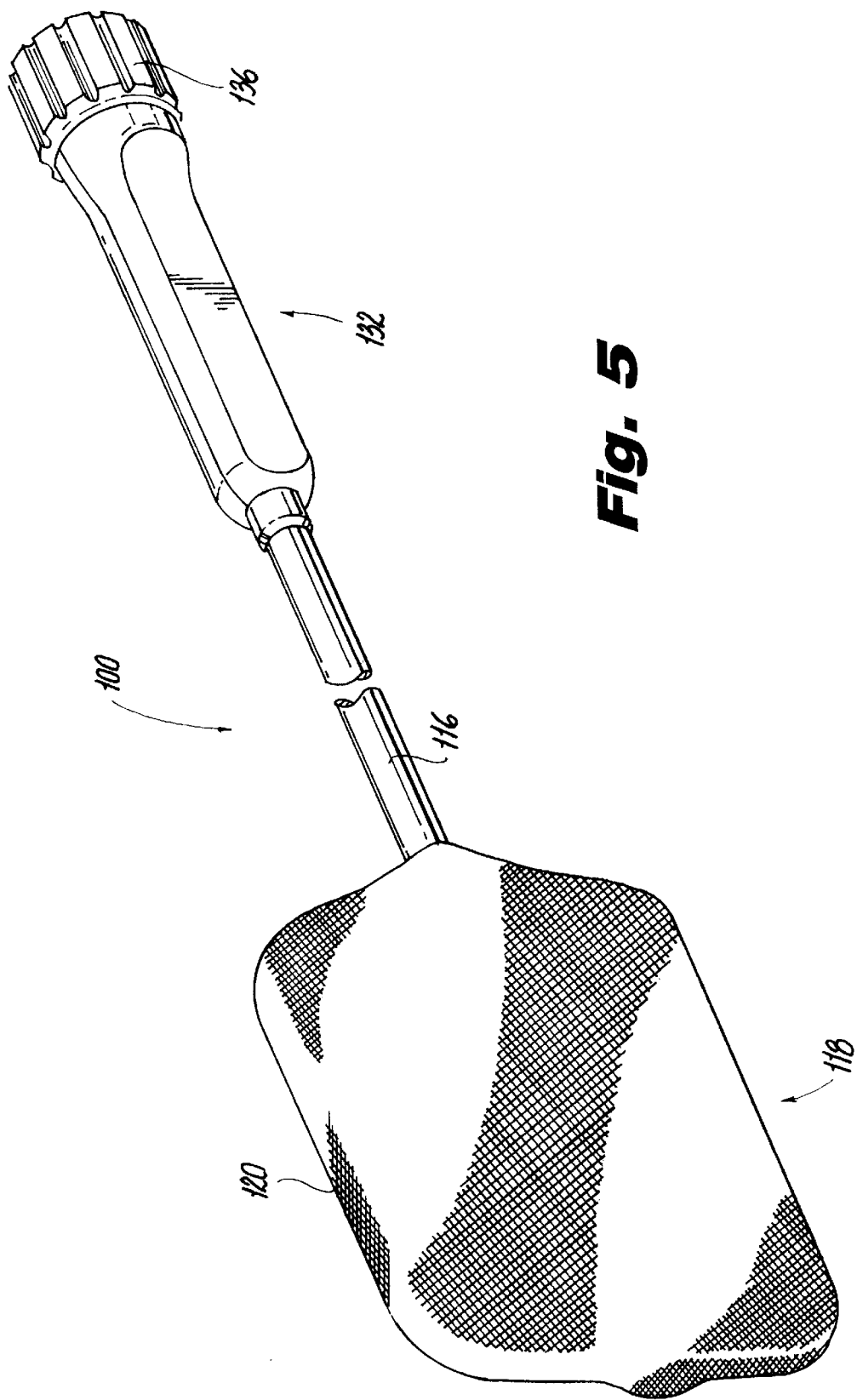
FIG. 5 is a perspective view of another preferred embodiment of a retractor assembly disposed in an open position.

In FIGS. 5–7, there is shown at 100 an alternative embodiment of a surgical retractor. Retractor 100 is utilized in a similar manner to retractor 10 heretofore described. Retractor 100 includes expandable retractor assembly 118 covered by expandable sheath 120, an elongate body portion which includes outer tube 116, and handle assembly 132. Similar to the previous embodiment adjusting knob 136 is provided at the proximal end portion of the handle 132 to deploy retractor assembly 118.

FIGS. 6–7 illustrate the structural configuration of surgical retractor 100. Retractor assembly 118 consists of a rigid stabilizing member 122 oriented along a longitudinal axis having a proximal end portion and a distal end portion. The proximal end of the stabilizing member 122 is dimensioned to be slidably received in outer tube 116. Retractor assembly 118 further consists of a pair of resilient bands 124a and 124b having strengthening ribs 125a and 125b, a pair of medial arms 130a and 130b, and a pair of proximal arms 132a and 132b.

The following description is referenced to one side of the retractor assembly 118, but is applicable to a retractor having a symmetrical configuration, as shown. Resilient band 124a is preferably formed from stainless steel, shape memory alloy or flexible polymer. In an unstressed state, resilient band 124a consists of a distal straight portion, a medial portion having a radiused elbow configuration, and a proximal straight portion. The distal portion of resilient member 124a is adapted to be pivotably mounted to the distal end portion of stabilizing member 122, and pivotably retained therein by distal retaining pin 126.

Medial arm 130a has a first end pivotably mounted to stabilizing member 122 and retained therein by a medial retaining pin 134, and a second end pivotably connected to the proximal end portion of resilient band 124a, and retained therein by juncture retaining pin 136a. Proximal arm 132a has a first end pivotably mounted to driving rod 114 and retained therein by proximal retaining pin 138. A second end of proximal arm 132a is pivotably connected at the juncture of medial arm 130a and the distal end portion of resilient band 124a and retained by juncture retaining pin 116a.

FIG. 7 illustrates the Structural configuration of surgical retractor 100 in a collapsed position, wherein driving rod 114 is moved proximally to collapse the frame structure of retractor assembly 118. In this embodiment, distal pin 126 and medial pin 134 are fixed with respect to the stabilizing member. Proximal pin 138 is fixed with respect to driving rod 114. Juncture pin 136a traces an arcuate path with respect to proximal pin 138 and medial pin 134 respectively. Progressive deployment or opening of the retractor is achieved by distal displacement of driving rod 114. At the proximalmost position of driving rod 114, as illustrated in FIG. 7, juncture pin 136a is positioned at the closest transverse distance to stabilizing member 122, placing retractor assembly 118 in the closed position. The proximal and medial arms 130a–b and 132a–b are positioned within a recess formed in the stabilizing member. At the distalmost position of driving rod 114 as illustrated in FIG. 6, juncture pin 136a is at the furthest transverse distance from stabilizing member 122, placing retractor 118 in the fully deployed position. At such a time, sheath 120 is fully expanded and defines a substantially rectangular manipulation surface suitable for manipulating body tissue as well as organs and vessels.

Figure 9:
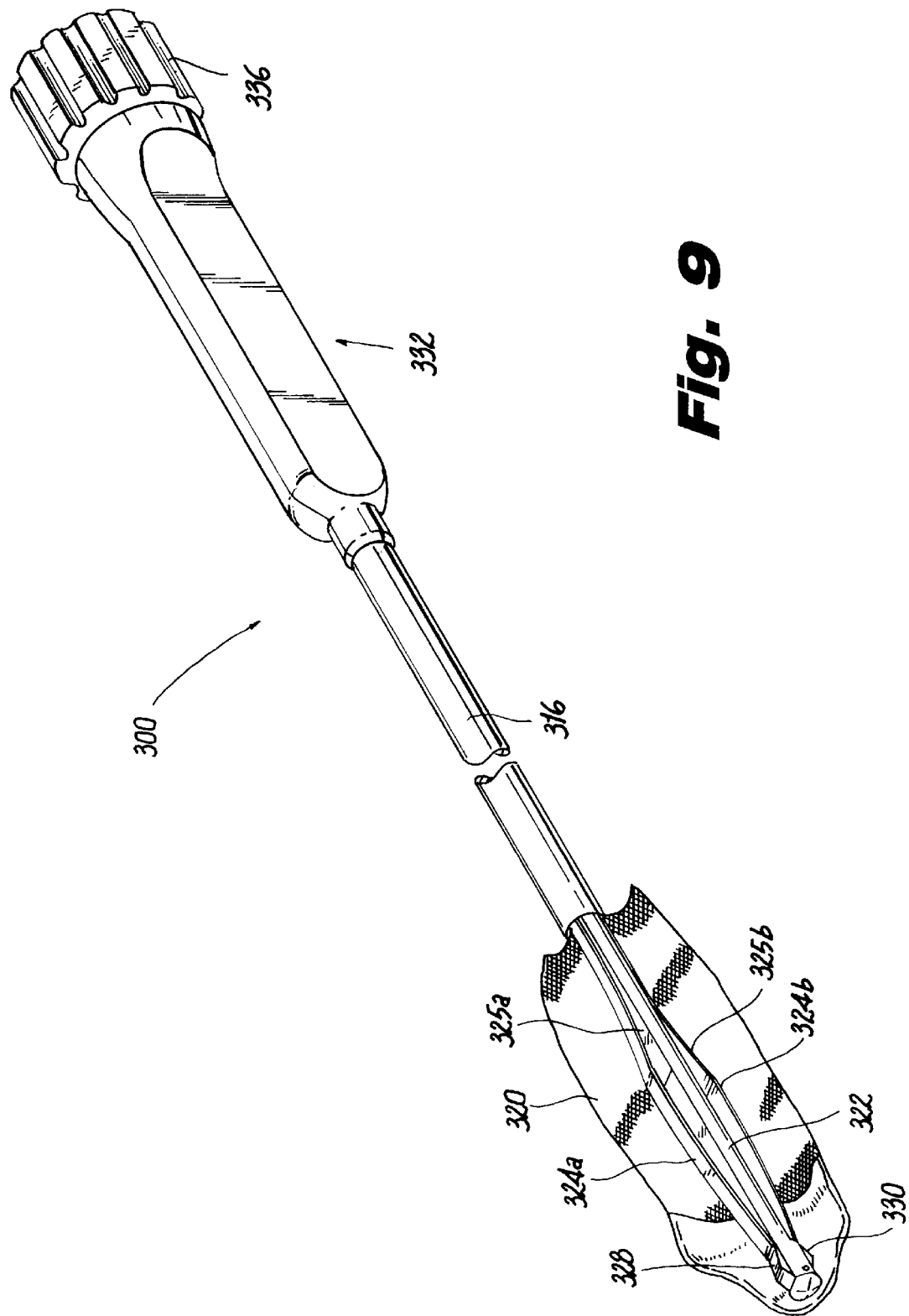
FIG. 9 is a perspective view of the retractor of FIG. 8 in a substantially closed position, shown with a substantially sheath partially cut away.

Turning to FIGS. 8–9, another preferred embodiment of the surgical retractor is shown. Retractor 300 is utilized in a similar manner to retractor 10 and 100 heretofore described. Retractor 300 includes expandable retractor assembly 318 covered by expandable tubular sheath 320, an elongate body portion which includes outer tube 316, and handle assembly 332. Expandable retractor 318 is progressively deployed by adjusting knob 336 provided at the proximal end portion of handle 332, similar to the manner described above.

Retractor assembly 318 includes a stabilizing member 322 depending longitudinally from outer tube 316 and fixed thereto with retaining pin 357. A pair of resilient bands 324a and 324b are pivotably connected at the distal portion of stabilizing member 322 by hinges 328 and 330, and retained therein by retaining pin 326. The resilient bands 324a and 324b are preferably formed of stainless steel or other resilient material. In the deployed configuration, the shape of resilient bands 324a and 324b is a substantially rectangular or trapezoidal configuration. Resilient bands 324a and 324b are provided at medial portions thereof with stabilizing rib members 325a and 325b. In the deployed configuration, rib members 325a and 325b are substantially parallel to stabilizing member 322 and are generally parallel with the longitudinal axis of the instrument. Rib members 325a and 325b provide resilient bands 324a and 324b with a deployed configuration that is predictable in shape and resists deformation during manipulation of heavy organs or tissue structures within the body cavity.

With continued reference to FIG. 8, the proximal end portions of resilient bands 324a and 324b are connected to the distal end of driving shaft 314 by retaining pin 352. Driving shaft 314 is configured for reciprocal longitudinal displacement within outer tube 316, and actuated by the actuator mechanism which includes knob 336, substantially as described hereinabove with respect to surgical retractor 10.

Attention is now directed to FIG. 9, which illustrates of retractor assembly 318 in the collapsed position. In the collapsed position, drive shaft 314 is in the proximalmost position and resilient bands 324a and 324b in a substantial straightened, longitudinal position and at least partially disposed in outer tube 316. Stabilizing member 322 is further provided with a pair of channels 323 to receive stabilizing ribs 325a and 325b when the resilient bands 324a and 324b are in the collapsed configuration. Retractor 300 can also be provided with a slidable protective sleeve to surround the sheath during insertion and/or withdrawal from a cannula.

Figure 10:
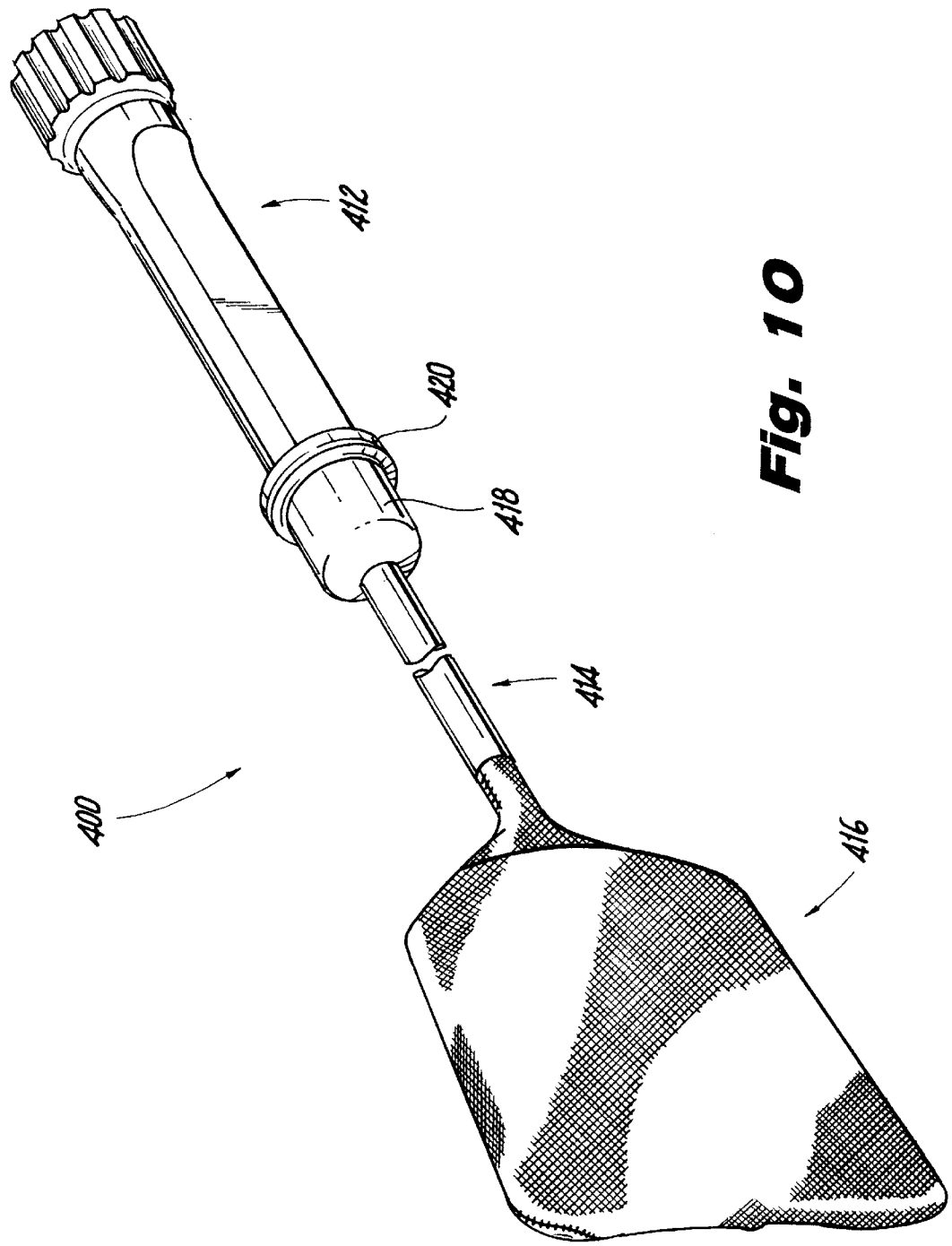
FIG. 10 is a perspective view of another preferred embodiment of a retractor assembly disposed in an open position.

FIGS. 10–17 illustrate an alternate embodiment of the surgical retractor shown generally as 400. Briefly, as illustrated in FIG. 10, retractor 400 includes a handle assembly 412, elongated body portion 414, a expandable retractor assembly 416 and a tubular sheath 470. Optionally, a cover tube 418 may be slidably disposed about elongated body portion 414. A gripping member 420 is formed at the proximal end of cover tube 418 to facilitate longitudinal movement of the cover tube 418 about the elongated body portion 414.

Figure 11:
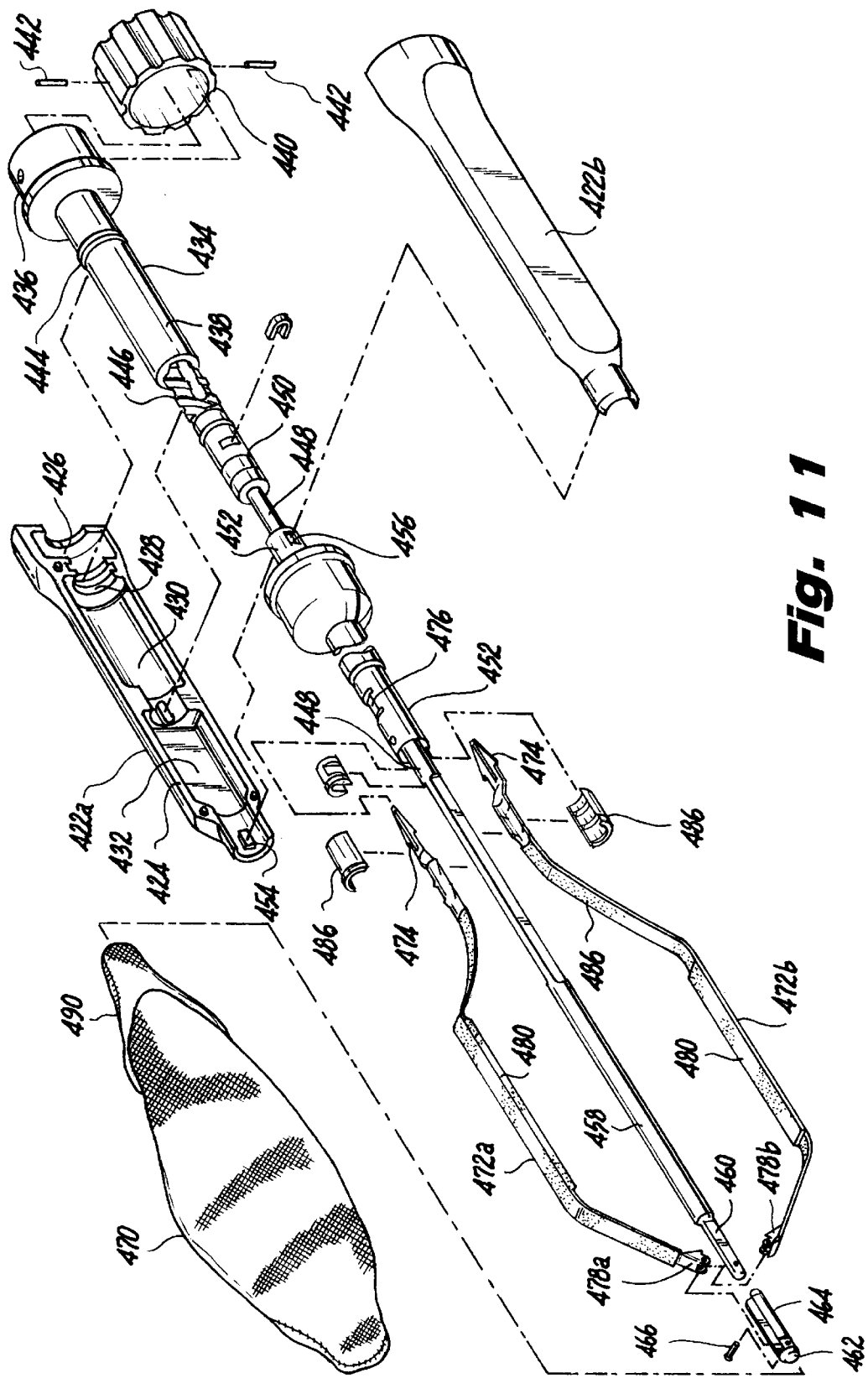
FIG. 11 is an exploded perspective view of the surgical retractor of FIG. 10.

FIG. 11 illustrates a perspective view of surgical retractor 400 with parts separated. The handle assembly 412 includes right and left hemi-sections 422a and 422b having a stepped longitudinal bore 424 extending therethrough. The longitudinal bore 424 is defined by a proximal chamber 426, a circumferential groove 428, a medial chamber 430, and a distal chamber 432, which enclose an actuation mechanism for manipulating the retractor assembly 416.

The actuator mechanism includes a rotatable screw member 434 having a proximal portion 436 of increased diameter and a distal cylindrical portion 438 having inner threads (not shown). A rotatable knob 440 is secured to proximal portion 436 by pins 442 to facilitate rotation of the rotatable screw member 434. An annular retaining member 444 formed about distal cylindrical portion 438 prevents longitudinal movement of the rotatable screw member 434. A driving screw 446 engages the inner screw threads of the cylindrical portion 438, such that upon rotation of rotatable knob 440, driving screw 446 is moved axially within the longitudinal bore 424. A driving rod 448 is coupled to the distal end of driving screw 446 by a coupling member 450 which translates the rotary linear movement of the driving screw 446 into linear movement of the drive rod 448. Drive rod 448 extends from the actuation mechanism through the elongated body 414 to the expandable retractor assembly 416.

The elongated body portion 414 includes an outer tube 452 which is fixedly connected at its proximal end between hemi-sections 422a and 422b of handle assembly 412. A pair of projections 454 formed within the distal end of handle assembly 412 are configured to be received within openings 456 formed in the proximal end of the outer tube 452 to secure the outer tube 452 to the handle assembly 412. The outer tube 452 has a longitudinal axis which is axially aligned with the longitudinal axis of the drive rod 448 to permit the drive rod 448 to be reciprocated within the outer tube.

Referring also to FIGS. 12–15, expandable retractor assembly 416 includes a central stabilizing member 458 which provides support to the retractor assembly 416 during manipulation of internal organs and body tissue. The stabilizing member 458 is axially aligned with the outer tube 452 and includes a proximal end which is connected to the drive rod 448. Although the stabilizing member 458 is illustrated as being monolithically formed with the drive rod 448, the parts may be separately constructed and coupled together via any known coupling.

The distal end of the stabilizing member 458 is formed with a pair of diametrically opposed flats 460. A cover member 462 having a pair of legs 464 positioned adjacent the flats 460 is pivotally secured about a pivot pin 466 at the distal end of the stabilizing member 458. The cover member 462 has a rounded distal face and smooth sidewalls to prevent tearing of the tubular sheath 470 and prevent trauma to internal organs and body tissue.

A pair of resilient band members 472a and 472b have a proximal end 474 configured to be fixedly received within an opening 476 formed in the distal end of the outer tube 452. The distal end of the resilient band members 472a and 472b include hinge members 478a and 478b, respectively which are pivotably mounted about pivot pin 426 on opposite sides of the stabilizing member 458. The hinge members 478a and 478b are covered by respective legs 464 of cover member 462 to provide a smooth distal end to the retractor assembly. Each band may include at least one stabilizing rib 480 to provide increased strength along a portion of the band. For example, the stabilizing rib may include an area of increased thickness or, as shown, a perpendicularly oriented strip extending along a portion of the length of the resilient band.

Resilient bands 472a and 472b are preferably formed of stainless steel or other flexible resilient material, such as shape memory alloy or a flexible polymer. An insulative plastic wrap 486 (FIG. 14) may be provided about the resilient bands to prevent tearing of the sheath 470 and trauma to internal organs and body tissue. In the present embodiment, the resilient bands are movable between a closed position in which the stabilizing member 458 is advanced distally and a deployed position in which the stabilizing member is retracted proximally. In the deployed position, the resilient bands 472a and 472b are preferably symmetrical about the stabilizing member 458 and together have a generally rectangular configuration. Sidewalls 482 and 484 of the rectangular configuration are defined by the location of the stabilizing ribs 480 on the resilient bands. Alternately, other configurations may be provided by changing the position of the stabilizing ribs on the resilient bands or by providing multiple ribs on each band. For example, multiple stabilizing ribs 480 may be spaced along each resilient band 472a and 472b to form an octagonal shape (FIG. 13A) or a decagonal shape (FIG. 13B). In the closed position, the resilient bands 472a and 472b are substantially straight and extend proximally from the pivot member 466 in close approximation with the stabilizing member 458 to opening 476 in outer tube 452. The resilient bands 472a and 472b are preferably fabricated with a rectangular cross-section to strengthen the bands in the deployed position.

The expandable sheath 470 is preferably fabricated from a textile material such as surgical mesh, cloth or nylon but may also be fabricated from an elastomeric material such as, for example, latex. The sheath preferably has a double walled proximal end 490 to resist tearing, and is configured to enclose the resilient bands 472a and 472b in the expanded condition.

As illustrated in FIG. 17, the proximal end of the sheath 470 is preferably retained between a locking collar 486 and an outer surface of the proximal ends of resilient bands 472a and 472b, which are positioned within a distal end of the outer tube 452. The proximal end of each band includes a convex portion 492 and a tapered portion 494 (See FIG. 11). The convex portion 492 engages an outer rounded surface of the stabilizing member 458 and permits relative sliding movement therebetween. The opening 476 in the outer tube 452 includes a proximal and a distal slot 496 and 498 and transversely extending projections 500. Tapered portion 494 of the bands is fed through distal slot 498 over the projections 500 and through proximal slot 496 into the outer tube 452 and is thereby retained in position.

Figure 12:
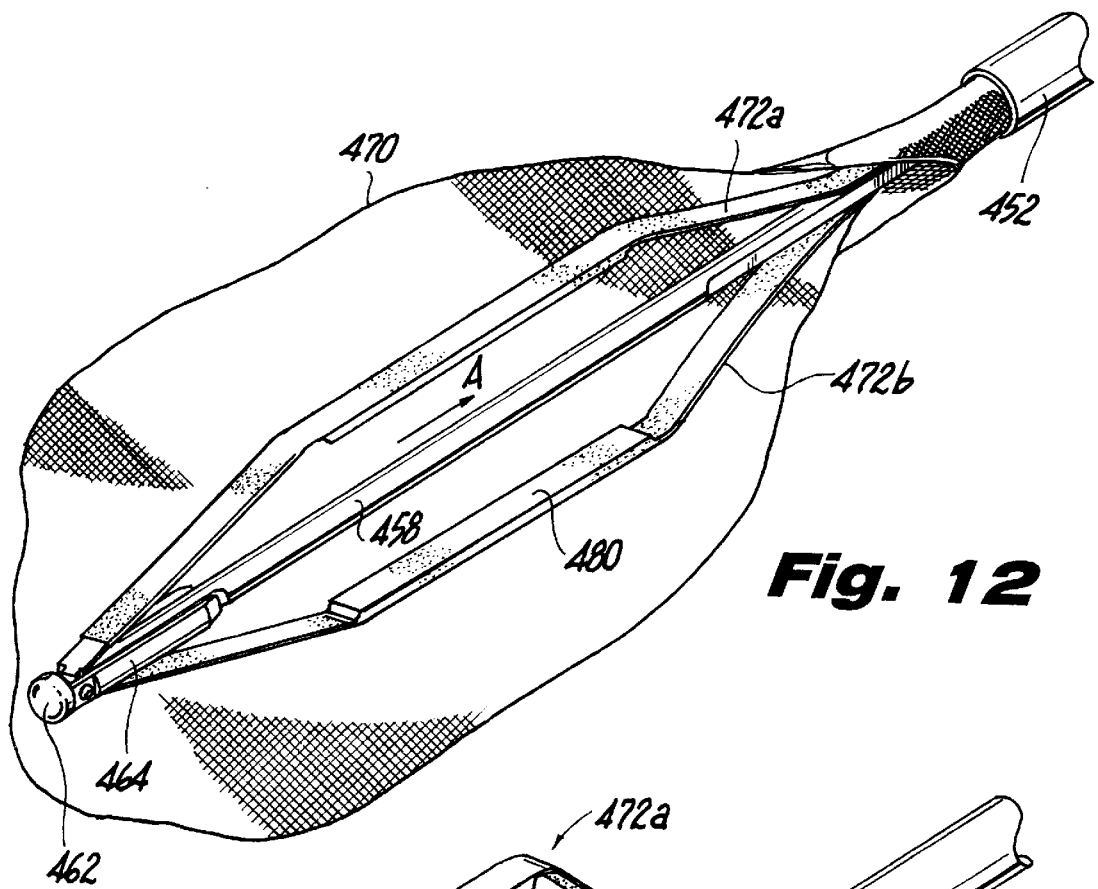
FIG. 12 is a perspective view of the distal end of the surgical retractor of FIG. 10 with a portion of the sheath removed in a partially open position.
Figure 13:
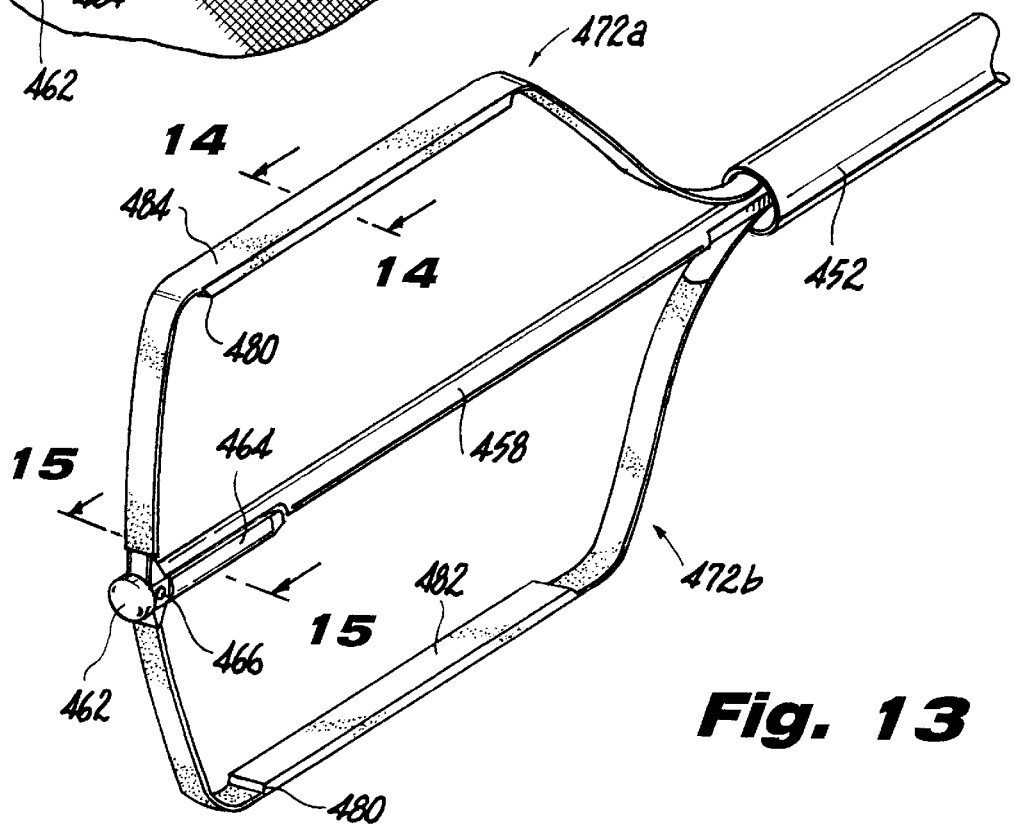
FIG. 13 is a perspective view of the distal end of the surgical retractor of FIG. 10 in the open position with the sheath removed.
Figure 13B:
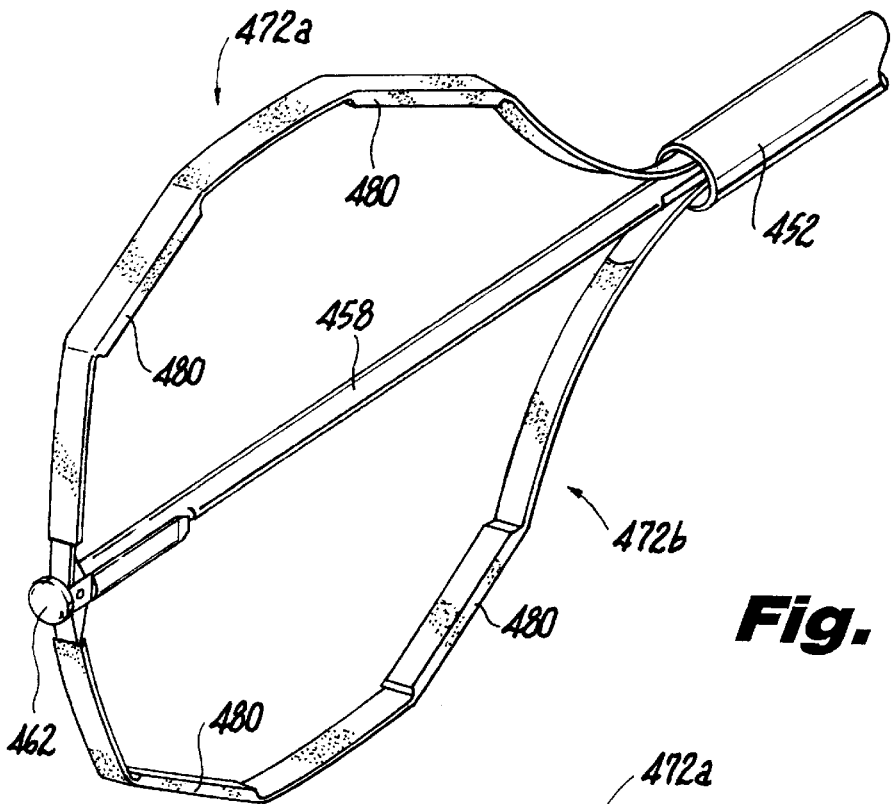
FIG. 13B is a perspective view of another alternate embodiment of the distal end of the surgical retractor in the open position with the sheath removed.
Figure 13A:
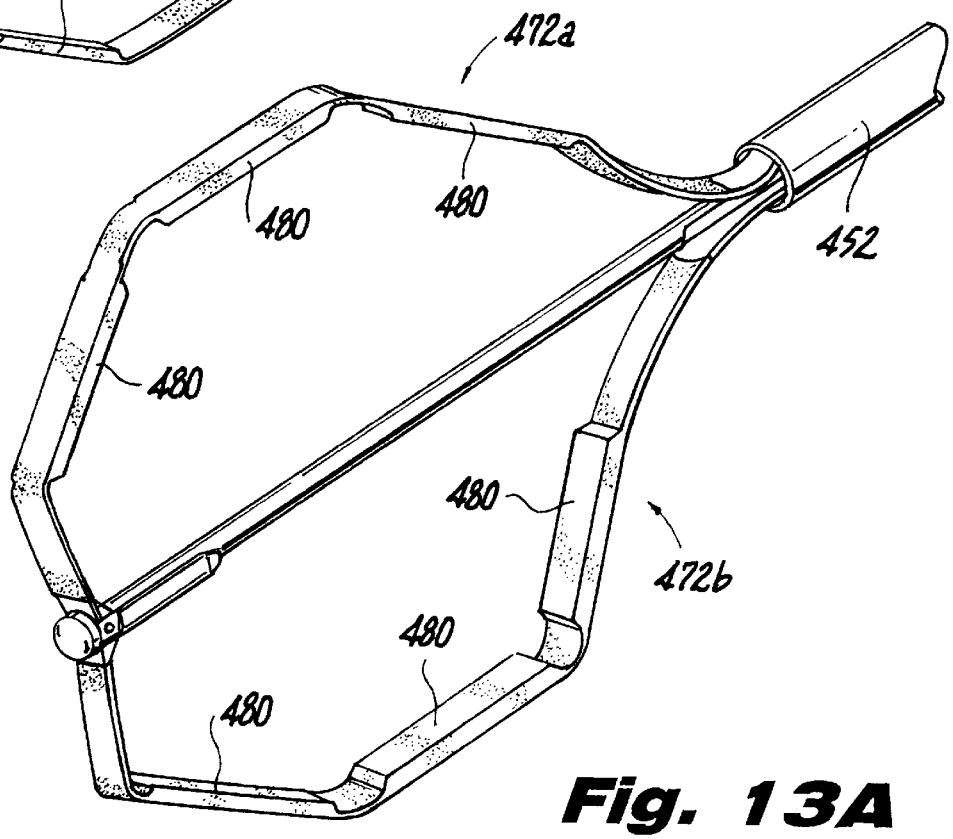
FIG. 13A is a perspective view of an alternate embodiment of the distal end of the surgical retractor in the open position with the sheath removed.

With reference to FIGS. 11–13, operation of retractor 400 will now be described. When it is desired to move the retractor assembly 416 from the closed to the expanded position, rotatable knob 440 is rotated to retract driving screw 446 proximally within longitudinal bore 424. The rotary linear movement is translated to linear proximal movement of the drive rod 448 via coupling 450 which results in corresponding proximal movement of the stabilizing member 458, as indicated by arrow "A" in FIG. 11. As stabilizing member 458 is retracted, resilient bands 472a and 472b are deflected outwardly. The shape of deflection is controlled by the stabilizing ribs 480 on the resilient bands 472a and 472b. The distal ends of the bands pivot on hinge members 478a and 478b about pivot member 466, such that in the fully retracted position of the stabilizing member 458, the bands form a generally rectangular configuration.

FIG. 18 illustrates a surgical retractor kit which may include any of the above-described surgical retractors, but will be described with reference to surgical retractor 400. The surgical retractor kit includes a surgical package 520, surgical retractor 400, a base panel 522, and a static barrier 524. Surgical package 520 is preferably blow molded from a suitable plastic material and includes indentations configured to receive a surgical retractor in an expanded position. The static barrier 524 defines a pocket or cover dimensioned to enclose the retractor assembly 416 in the expanded position. Preferably, the static barrier 524 is constructed from anti-static grade Tyvek® (Dupont Inc., Reference No. 1085D), or some other suitable material capable of preventing static electric charge buildup on the tubular sheath 470. Base panel 522 is also preferably constructed from Tyvek® and is sealed about its periphery to edge 526 of package 520 using an adhesive or by heat-sealing.

Figure 20:
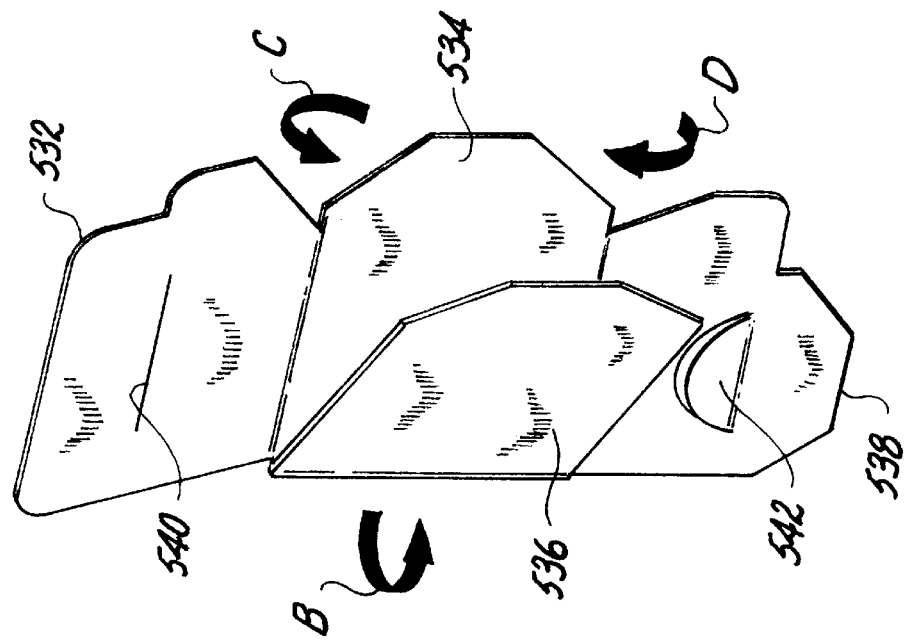
FIG. 20 is a perspective view of the foldable cutout shown in FIG. 19 in a partially folded condition.
Figure 19:
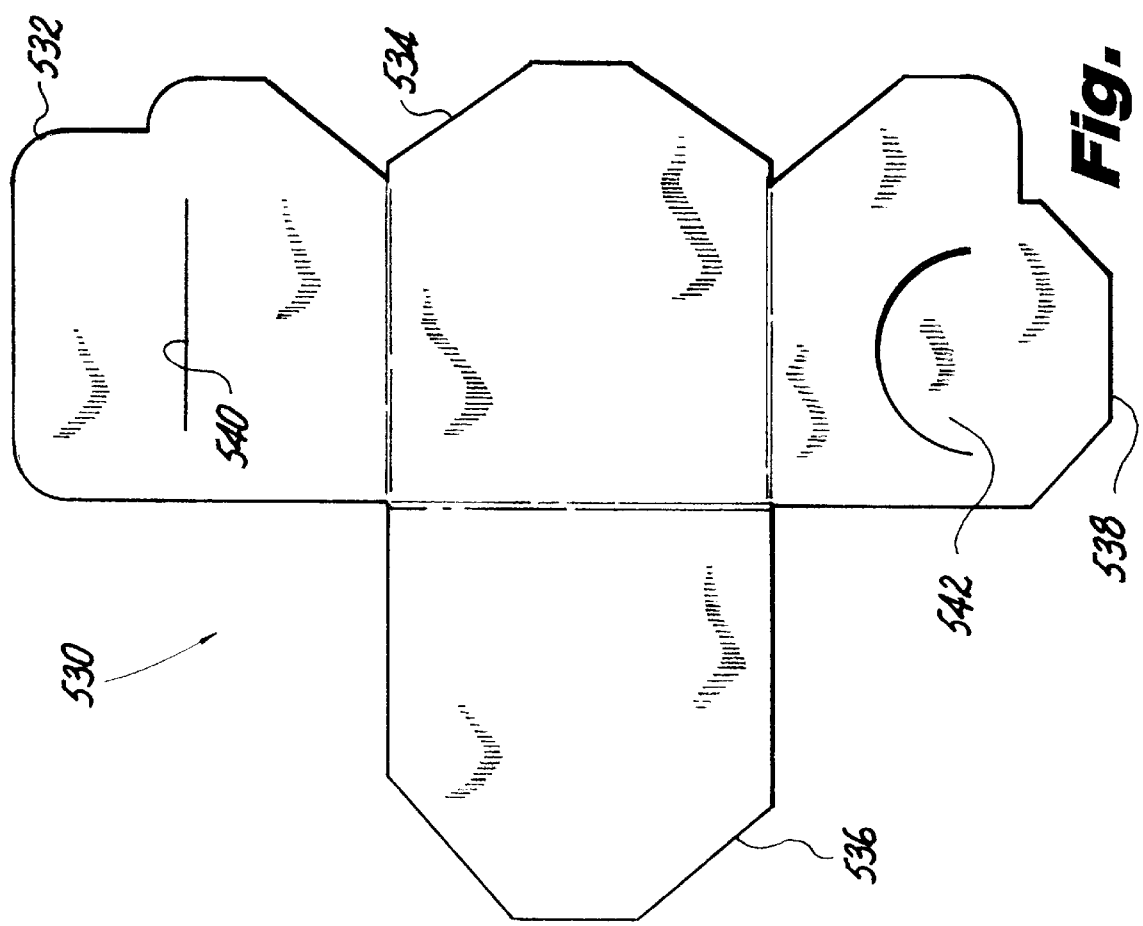
FIG. 19 is a top view of the foldable cutout for constructing the static barrier.

Referring to FIGS. 19 and 20, the static barrier 524 may be constructed from a planar foldable cutout 530 having a top panel 532, a center panel 534, a side panel 536, and a bottom panel 538. The top panel 532 has a linear slit 540 and the bottom panel 538 has a semi-circular tab 542. To construct static barrier 524, side panel 536 is folded over center panel 534, as indicated by arrow "B" in FIG. 20. Next, top panel 532 is folded over side panel 536, as indicated by arrow "C", and bottom panel 538 is folded over top panel 532, as indicated by arrow "D". Tab 542 is inserted through slit 540 to retain the static barrier in the folded position.

It will be understood that various modifications may be made to the embodiments disclosed herein. For example, the resilient bands may be oriented with respect to each other at greater or less than 180° resulting in a three dimensional retracting surface as surgical conditions require. Also, while the static barrier disclosed herein is shown in conjunction with a surgical retractor, the barrier can be used with other surgical instruments, wherein it is desirable to reduce or eliminate static charges. Therefore, the above description should not be construed as limiting, but merely as exemplifications of preferred embodiments. Those skilled in the art will envision other modifications within the scope and spirit of the claims appended hereto.

What is claimed is:

1. A surgical retractor kit comprising:
   a) a surgical package having an indentation configured to receive a surgical retractor and an opening;
   b) a surgical retractor having a handle member, an elongated body portion, a retractor assembly and a sheath configured to enclose the retractor assembly;
   c) a base panel configured to enclose the surgical package opening; and
   d) a static barrier configured to enclose at least a portion of the retractor assembly and sheath.

2. A surgical retractor kit according to claim 1, wherein the static barrier is constructed from Tyvek®.

3. A surgical retractor kit according to claim 1, wherein the retractor assembly is movable from a closed position to an expanded position, and the static barrier is configured to enclose the retractor assembly in the expanded position.

4. A surgical retractor kit according to claim 1, wherein the base panel is adhesively sealed about the periphery of the surgical package opening.

5. A surgical retractor kit according to claim 2, wherein the base panel is constructed from Tyvek®.

6. A method for packaging a surgical instrument comprising:
   a) providing a surgical package configured to receive a surgical instrument;
   b) providing a surgical instrument having a proximal end and a distal end, the distal end having a mechanism for performing a surgical procedure;

c) providing a static barrier configured to at least partially enclose the mechanism of the surgical instrument;

d) positioning the static barrier to at least partially enclose the mechanism of the surgical instrument; and e) positioning the surgical instrument and static barrier in the package.

7. A method according to claim 6, wherein the surgical instrument is a surgical retractor and the mechanism is a retractor assembly.

8. A method according to claim 7, wherein the surgical retractor further includes a sheath positioned about the retractor assembly, and wherein the static barrier is positioned about the sheath.

9. A method according to claim 6, further including the step of constructing the static barrier from Tyvek®.

10. A method according to claim 6, wherein the package is formed with an opening configured to permit passage of the surgical instrument, and wherein the method further includes the step of providing a closure member configured to close the package opening.

* * * * *